United States Patent [19]

Grantham

[11] Patent Number: 4,754,782

[45] Date of Patent: Jul. 5, 1988

[54] HOSE ASSEMBLY & CLIP THEREFOR

[75] Inventor: Rodger P. Grantham, Springfield, Mo.

[73] Assignee: Dayco Products, Inc., Dayton, Ohio

[21] Appl. No.: 910,541

[22] Filed: Sep. 23, 1986

[51] Int. Cl.$^4$ ............................................. F16L 39/02
[52] U.S. Cl. .................................. 138/109; 138/113; 138/115; 285/133.1; 141/392
[58] Field of Search ............... 138/111, 113, 109, 114, 138/115, 148, 149; 285/133.1, 133.2; 141/392

[56] References Cited

U.S. PATENT DOCUMENTS

| 2,214,708 | 9/1940  | Mayne et al. | 141/392 |
| 2,650,112 | 8/1953  | Kinkead | 285/133.1 X |
| 2,956,586 | 10/1960 | Zeigler et al. | 285/133.1 |
| 2,959,193 | 11/1960 | Guldenzoph et al. | 285/133.1 X |
| 3,590,855 | 7/1971  | Wollen et al. | 138/111 |
| 3,734,652 | 5/1973  | Barnett | 285/133.1 X |
| 3,980,112 | 9/1976  | Basham | 141/392 |
| 4,067,596 | 1/1978  | Kellner et al. | 285/133.2 |
| 4,445,332 | 5/1984  | Thies et al. | 285/133.1 |
| 4,522,234 | 6/1985  | Kellner et al. | 138/113 |
| 4,615,359 | 10/1986 | Affo et al. | 138/113 X |
| 4,676,563 | 6/1987  | Curlett et al. | 285/133.2 |

Primary Examiner—James E. Bryant, III
Attorney, Agent, or Firm—Joseph V. Tassone

[57] ABSTRACT

A hose assembly, clip structure therefor and method of making the same are provided, the hose assembly having fluid passages therein for respectively conveying a volatile liquid in one direction to a container and returning the vapors of the volatile liquid from the container, the assembly comprising a flexible inner hose having an outer peripheral surface and defining an inner one of the passages, a flexible outer hose having an inner peripheral surface and being disposed around said inner hose, the inner peripheral surface of the outer hose and the outer peripheral surface of the inner hose defining an outer one of the passages, a coupling fixed to one end portion of the outer hose, a tubular fitting fixed to an end portion of the inner hose, and a clip holding the fitting and the end portion of the inner hose substantially concentrically within the coupling and the outer hose to define a continuation of the outer passage, the clip comprising a generally cylindrical one-piece C-shaped member that extends in a circular arc that is greater than 180° and having substantially concentric inner and outer surfaces respectively engaging the fitting and the coupling, the C-shaped member having opposite ends spaced from each other to define an opening between the surfaces thereof in communication with the outer passage on opposite sides of the clip for fluid flow therethrough.

9 Claims, 2 Drawing Sheets

HOSE ASSEMBLY & CLIP THEREFOR

BACKGROUND OF THE INVENTION

1. Field of the Invention

This invention relates to a new hose assembly and a new clip means therefor as well as to a new method of making such a hose assembly.

2. Prior Art Statement

It is known to provide a hose assembly having fluid passages therein for respectively conveying a volatile liquid in one direction to a container and returning vapors of the volatile liquid from the container, the assembly comprising a flexible inner hose having an outer peripheral surface and defining an inner one of the passages, a flexible outer hose having an inner peripheral surface and being disposed around the inner hose, the inner peripheral surface of the outer hose and the outer peripheral surface of the inner hose defining an outer one of the passages, a coupling fixed to one end portion of the outer hose, a tubular fitting fixed to an end portion of the inner hose, and clip means holding the fitting and the end portion of the inner hose substantially concentrically within the coupling and the outer hose to define a continuation of the outer passage. For example, see the U.S. Pat. No. 3,980,112 to Basham.

SUMMARY OF THE INVENTION

It is one feature of this invention to provide a new hose assembly having a unique clip means for holding parts of the hose assembly substantially in concentric relation.

In particular, it was found according to the teachings of this invention that the clip means can comprise a generally cylindrical member having substantially concentric inner and outer surfaces for respectively engaging a fitting and a coupling of the hose assembly and have at least one opening means between the surfaces thereof in communication with an outer passage of the hose assembly on opposite sides of the clip means for fluid flow therethrough.

For example, one embodiment of this invention provides a hose assembly having fluid passages therein for respectively conveying a volatile liquid in one direction to a container and returning vapors of the volatile liquid from the container, the assembly comprising a flexible inner hose having an outer peripheral surface and defining an inner one of the passages, a flexible outer hose having an inner peripheral surface and being disposed around the inner hose, the inner peripheral surface of the outer hose and the outer peripheral surface of the inner hose defining an outer one of the passages, a coupling fixed to one end portion of the outer hose, a tubular fitting fixed to one end portion of the inner hose, and clip means holding the fitting and the end portion of the inner hose substantially concentrically within the coupling and the outer hose to define a continuation of the outer passage, the clip means comprising a generally cylindrical one-piece C-shaped member that extends in a circular arc that is greater than 180° and having substantially concentric inner and outer surfaces respectively engaging the fitting and the coupling the C-shaped member having opposite ends spaced from each other to define an opening means between the surfaces thereof in communication with the outer passage on opposite sides of the clip means for fluid flow therethrough.

Accordingly, it is an object of this invention to provide a new hose assembly having fluid passages therein for respectively conveying a volatile liquid in one direction to a container and returning vapors of the volatile liquid from the container, the hose assembly of this invention having one or more of the novel features of this invention as set forth above or hereinafter shown or described.

Another object of this invention is to provide a new clip means for such a hose assembly or the like, the clip means of this invention having one or more of the novel features of this invention as set forth above or hereinafter shown or described.

Another object of this invention is to provide a new method of making such a hose assembly, the method of this invention having one or more of the novel features of this invention as set forth above or hereinafter shown or described.

Other objects, uses and advantages of this invention are apparent from a reading of this description which proceeds with reference to the accompanying drawings forming a part thereof and wherein:

DESCRIPTION OF THE PREFERRED EMBODIMENTS

Figure 1:
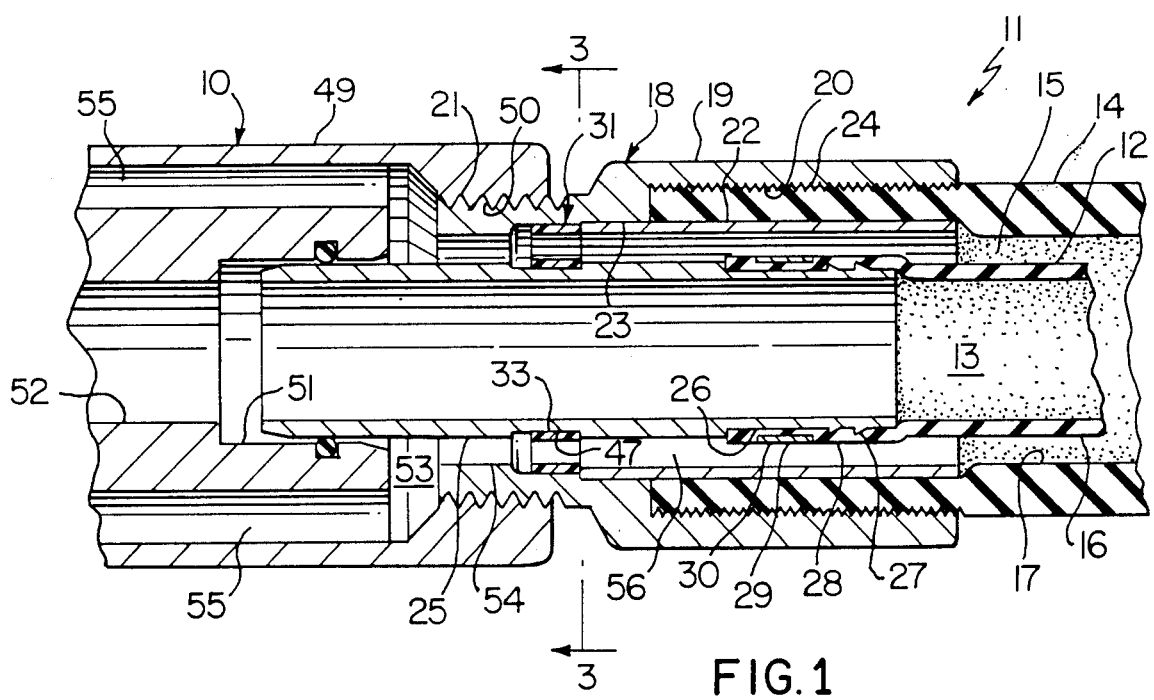
FIG. 1 is a fragmentary cross-sectional view of one embodiment of the new hose assembly of this invention.

While the various features of this invention are hereinafter illustrated and described as being particularly adapted to provide a hose assembly for conveying volatile fluids, it is to be understood that the various features of this invention can be utilized singly or in various combinations thereof to provide a hose assembly for other purposes as desired.

Therefore, this invention is not to be limited to only the embodiments illustrated in the drawings, because the drawings are merely utilized to illustrate one of the wide variety of uses of this invention.

Referring now to FIG. 1, the new hose assembly of this invention is generally indicated by the reference numeral 11 and is shown attached to a typical adapter 10 for the purpose of transferring a volatile liquid, such as gasoline, through the hose assembly into the adapter 10, and conveying vapors from the adapter 10 back through the assembly. The environment in which such hose assembly 11 is utilized is fully described in the above-referenced U.S. Pat. No. 3,980,112 and, therefore, this patent is being incorporated into this disclosure by this reference thereto.

The hose assembly 11 comprises a flexible inner hose 12 which defines an inner passage 13 that conveys the liquid, and a flexible outer hose 14 disposed concentrically around the hose 12. The hoses 12 and 14 are relatively sized so that they define an annular outer passage 15 therebetween; that is, between the outer cylindrical peripheral surface 16 of the inner hose 12 and the inner cylindrical peripheral surface 17 of the outer hose 14.

The hose assembly 11 further comprises a coupling, generally designated by reference numeral 18, and having an outer housing 19 of tubular configuration with integral serrations 20 defining an inside surface at one end and with integral male threads 21 on the outer surface of the other end, which is reduced in diameter. The coupling 18 also has a cylindrical tubular member 22 secured to the inner surface 23 of the housing 19 by welding or similar means, the member 22 being coextensive with the serrated portion of the housing. The outer hose 14 has an end portion 24 which is assembled to the coupling by inserting it between the serrations 20 and the member 22 and applying radially inward pressure to provide a tight seal. If desired, suitable sealing materials may be provided between the outer surface of end portion 24 and the serrations, and between the inner surface of the end portion and the member 22.

A cylindrical fitting 25 has a reduced diameter end section 26 with barb-like projections 27, the end section 26 being inserted within an end portion 28 of the inner hose 12. A clamp 29, in the form of a short segment of a cylinder, is disposed around the outer surface of the end portion 28 of the hose so that when tightened the clamp 29 secures the end portion 28 between the end section 26 of the fitting 25 and the clamp 29. Upon tightening, the clamp 29 has an outer diameter 30 approximately equal to that of the end portion 28 of the hose 12.

The coupling assembly as described to this point is the same as that of U.S. Pat. No. 3,980,112. The principal difference resides in the use of the clip means 31 of this invention which is installed between the inner and outer hoses 12 and 14 for the purpose of holding these hoses in axial and concentric relationship in a manner similar to the clip means of the aforementioned U.S. Pat. No. 3,980,112.

Figure 2:
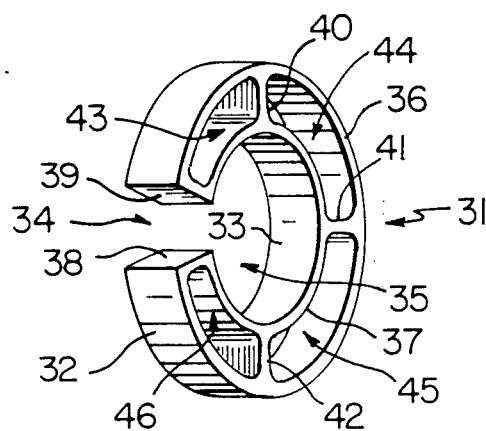
FIG. 2 is a perspective view of the new clip means of this invention that is utilized in the hose assembly of FIG. 1.
Figure 3:
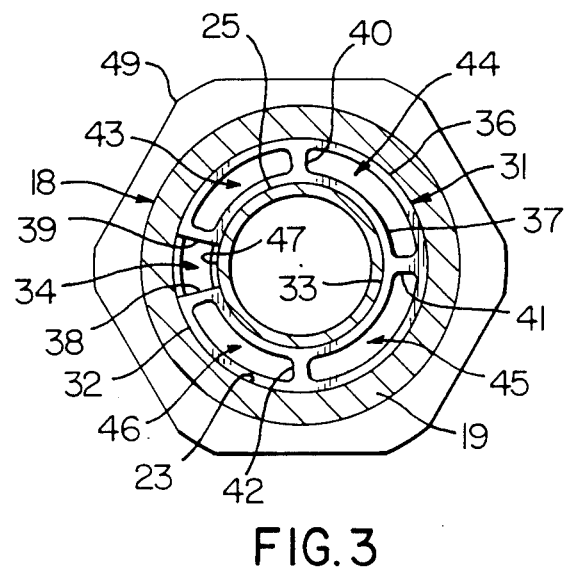
FIG. 3 is a cross-sectional view taken on line 3—3 of FIG. 1.
Figure 4:
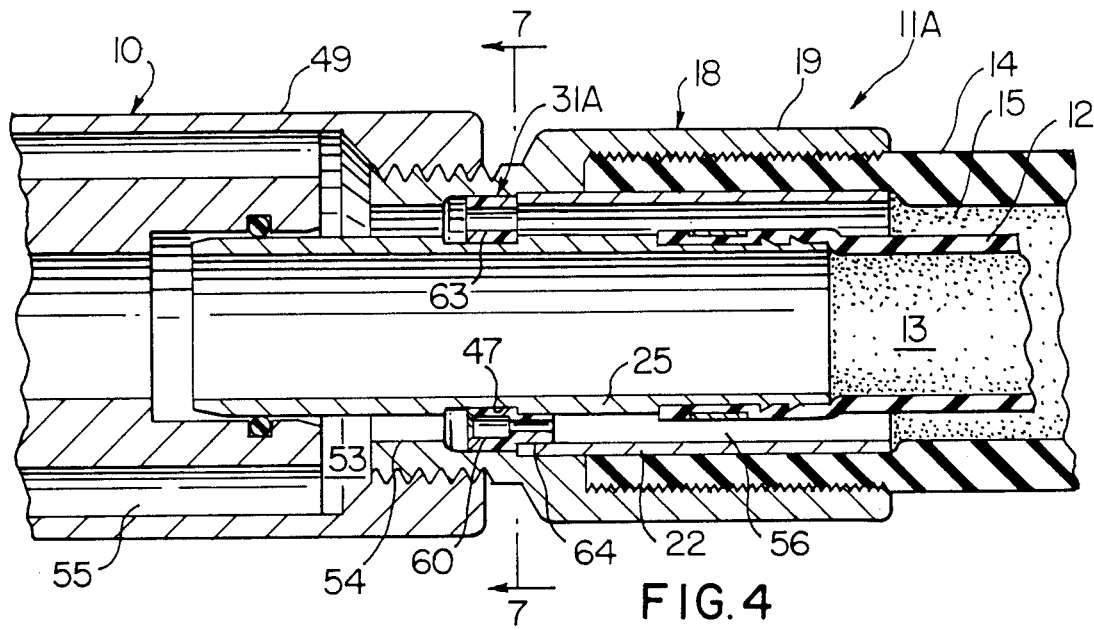
FIG. 4 is a fragmentary cross-sectional view of another embodiment of the new hose assembly of this invention.
Figure 5:
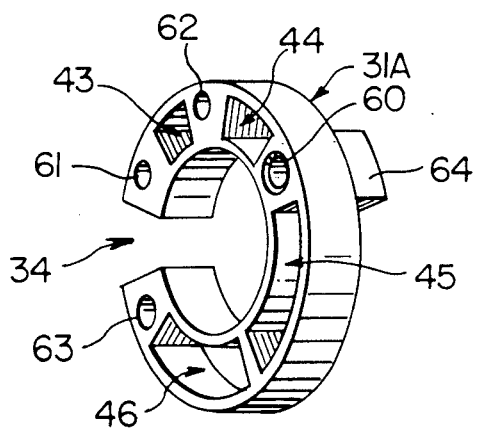
FIG. 5 is a perspective view of another new clip means of this invention that is utilized in the hose assembly of FIG. 4.
Figure 6:
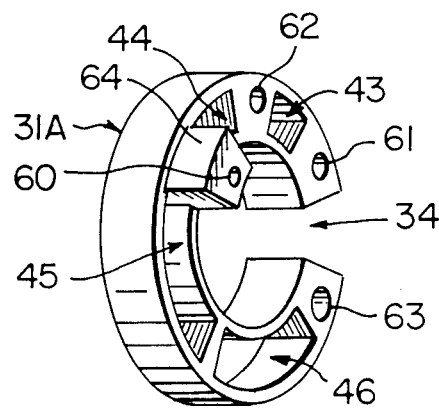
FIG. 6 is a perspective view of the other side of the clip means of FIG. 5.
Figure 7:
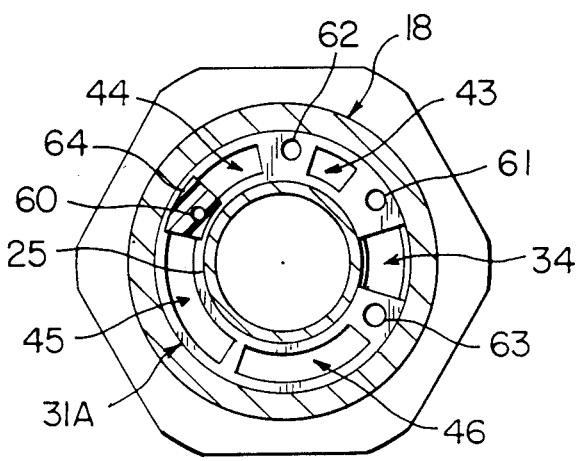
FIG. 7 is a cross-sectional view taken on line 7—7 of FIG. 4.

The clip means 31 of this invention is shown in detail in FIGS. 2 and 3 and is a generally cylindrical member which in one working embodiment thereof is approximately one-quarter inch in width, preferably formed of a polymeric material, such as nylon, ABS, polyethylene, EVA, or polypropylene, which lends itself to molding, casting, or other well-known processes. The material selected for the clip means 31 should be sufficiently resilient to enable it to be placed into position with a minimum of trouble, while being resistant to the fluids with which it is in contact, and possess the structural properties to retain the hoses in their desired relationship.

The clip means 31 has an outer surface 32 and a concentric inner surface 33, both of which are broken by a slot 34 that leads to the central opening 35 formed by the inner surface. Thus, the clip means 31 is actually comprised of an outer web 36 adjacent the outer surface 32, and an inner web 37 adjacent the inner surface 33, the webs 36 and 37 being joined together by exterior ribs 38 and 39 that form the slot 34, and also by interior ribs 40, 41 and 42. The inner and outer webs 37 and 36 and ribs 38-42 form a series of openings 43, 44, 45 and 46, which together with the slot 34 provide opening means through the clip means 31 for the purpose of conveying volatile vapors into the annular outer passage 15 of the assembly 11.

Thus, it can be seen that the clip means 31 can be a molded one-piece substantially C-shaped member that has opening means 34, 38-42 between the outer surface 32 and the inner surface 33 thereof for a purpose hereinafter described.

The clip means 31 is inserted between the inner and outer hoses 12 and 14 only indirectly as it actually is located so that its outer surface 32 contacts or engages the inner surface 23 of the outer housing 19 and its inner surface 33 is received within a reduced diameter notch or slot 47 extending continuously around the outer surface of the fitting 25 to contact or engage the fitting 25 as best shown in FIG. 3, the notch 47 cooperating with the natural resilience of the clip means 31 to prevent movement of the contacting members.

As described above, the inner hose 12 is secured to the fitting 25 and the outer hose 14 is secured between the tubular member 22 and the outer housing 19. The hoses 12 and 14 are thus retained in concentric relationship and create an annular passage 56 between the tubular member 22 and the inner fitting 25.

The hose assembly 11 is designed for use in conjunction with the adapter 10 which has a housing 49 equipped with internal or female threads 50 that cooperate with the external or male threads 21 in the reduced diameter portion of the housing 19. The adapter is similar to the adapter described in U.S. Pat. No. 3,980,112 and functions as described in that patent. A counterbore 51 is adapted to receive the outer end of fitting 25, and the counterbore is adjoined by a smaller diameter bore 52 to provide linear communication with the inner passage 13 that permits the liquid to flow into the adapter 10. A gap 53 is provided between the end of the housing 19 and the adapter 10 and communicates with an annular opening 54 between the fitting 25 and the housing 19. This permits the passage of the vapors back from the adapter 10 through the openings 55 in the housing 49 of the adapter 10, through the gap 53 and the opening 54, through the opening means 34, 38-42 in the clip means 31, into the annular passage 56 between tubular member 22 and inner fitting 25, and then into the annular outer passage 15 between the hoses 12 and 14 whereby the hose assembly 11 of this invention functions in the same manner of the hose assemblies set forth in the aforementioned U.S. Pat. No. 3,980,112 so that a further discussion of the operation of the hose assembly 11 and its environment need not be set forth.

Nevertheless, it can be seen that the hose assembly 11 of this invention has fluid passages 13 and 15 therein for respectively conveying a volatile liquid in one direction, such as to a container (not shown) and returning vapors of the volatile liquid from that container, the hose assembly 11 comprising a flexible inner hose 12 having an outer peripheral surface 16 defining an inner one 13 of the passages, a flexible outer hose 14 having an inner peripheral surface 17 and being disposed around the inner hose 12, the inner peripheral surface 17 of the outer hose 14 and the outer peripheral surface 16 of the inner hose 12 defining an outer one 15 of the passages, a coupling 18 fixed to one end portion 24 of the outer hose 14, a tubular fitting 25 fixed to an end portion 28 of the inner hose 12, and clip means 31 holding the fitting 25 and the end portion 28 of the inner hose 12 substantially concentrically within the coupling 18 and the outer hose 14 to define a continuation of the outer passage 15, the clip means 31 comprising a generally cylindrical member having substantially concentric inner and outer surfaces 33 and 32 respectively engaging the fitting 25 and the coupling 18 and having at least one opening means 34, 43, 44, 45 or 46 between the surfaces 32 and 33 thereof in communication with the outer passage 15 on opposite side of the clip means 31 for fluid flow therethrough.

While the opening means 34, 43–46 of the clip means 31 of this invention have been previously described as being solely for the purpose of conveying returning vapors of the volatile liquid therethrough and thereby forming a continuation of the outer passage 15 of the hose assembly 11, it is to be understood that one or more of such opening means 34, 43–46 of the clip means 31 of this invention can be utilized as interconnection means for interconnecting to additional structure of the hose assembly 11 if desired.

For example, reference is now made to FIGS. 4–8 wherein another embodiment of the hose assembly of this invention is generally indicated by the reference numeral 11A with parts thereof that are similar to the parts of the hose construction 11 of FIGS. 1–3 previously described being indicated by the same reference numerals.

Therefore, it can be seen that the hose assembly 11A is substantially identical to the hose assembly 11 previously described except that the same utilizes another new clip means 31A of this invention with the clip means 31A having the parts thereof that are similar to the parts of the clip means 31 previously described being indicated by the same reference numerals.

The clip means 31A also comprises a one-piece member formed of molded polymeric material and being substantially in a C-shape so as to function in substantially the same manner as the clip means 31 previously described for holding the parts of the hose assembly 11A in the concentric relationship as previously described and for providing the opening means 34, 43–46 for conveying the vapors of the volatile liquid and thereby providing a continuation of the outer passage 15 as previously described.

Figure 8:
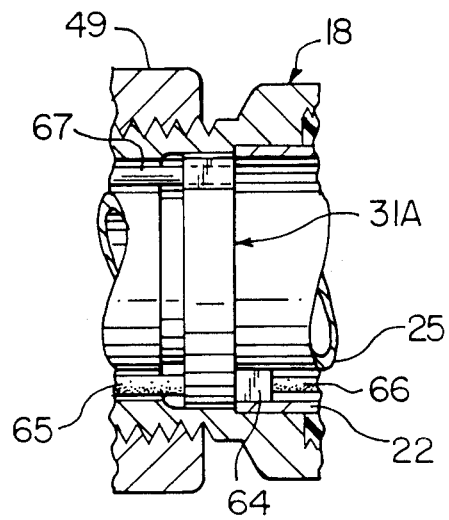
FIG. 8 is a schematic view illustrating how the clip means of FIG. 5 can be utilized with additional structure in the hose assembly of FIG. 4.

However, the clip means 31A additionally has interconnection means 60, 61, 62 and 63 for interconnecting to additional structure of the hose assembly 11A in the manner illustrated in FIG. 8 and hereinafter described, the interconnection means 60–63 merely comprising opening means of substantially circular cross section passing through the opposed sides of the clip means 31 with the interconnection means 60 also passing through an integral outwardly directed projection means 64 of the clip means 31A.

In this manner, the interconnection means 60 can be utilized to interconnect to any desirable structure, such as the smaller hoses 65 and 66 disposed in the passage 15 of the hose assembly 11A and being utilized to interconnect to a Venturi means in a manner well known in the art. The other interconnection means 61–63 can be utilized for interconnecting to other structure in the passage means 15, such as respectively receiving locating pins 67 therethrough in the manner illustrated in FIG. 8 to orient additional structure (not shown) on either side of the clip means 31A, such as the Venturi means that is interconnected to the hoses 65 and 66.

Also, it can be seen that the projection 64 of the clip means 31A of this invention is so constructed and arranged that the same is adapted to effectively be inserted between the fitting 25 and the sleeve 22 of the coupling 18 so as to be located at the bottom of the hose assembly 11A and thereby position the hoses 65 and 66 at the bottom thereof for a purpose well known in the art.

Therefore, it can be seen that the clip means 31A functions in the same manner as the clip means 31 previously described except that the same has additional interconnection means 60–63 for interconnecting to additional structure in the hose construction 11A whereby the clip means 31A is not only adapted to provide a continuation of the passage means 15 and hold the various parts of the hose assembly 11A in the concentric relation thereof, but also is adapted to position that other structure of the hose assembly 11A in desired positions thereof as previously described.

Therefore, it can be seen that this invention not only provides a new hose assembly and a new clip means for such a hose assembly or the like, but also this invention provides a new method of making such a hose assembly.

While the forms and methods of this invention now preferred have been illustrated and described as required by the Patent Statute, it is to be understood that other forms and method steps can be utilized and still fall within the scope of the appended claims wherein each claim sets forth what is believed to be known in each claim prior to this invention in the portion of each claim that is disposed before the terms "the improvement" and sets forth what is believed to be new in each claim according to this invention in the portion of each claim that is disposed after the terms "the improvement" whereby it is believed that each claim sets forth a novel, useful and unobvious invention within the purview of the Patent Statute.

What is claimed is:

1. In a hose assembly having fluid passages therein for respectively conveying a volatile liquid in one direction to a container and returning vapors of said volatile liquid from said container, said assembly comprising a flexible inner hose having an outer peripheral surface and defining an inner one of said passages, a flexible outer hose having an inner peripheral surface and being disposed around said inner hose, said inner peripheral surface of said outer hose and said outer peripheral surface of said inner hose defining an outer one of said passages, a coupling fixed to one end portion of said outer hose, a tubular fitting fixed to an end portion of said inner hose, and clip means holding said fitting and said end portion of said inner hose substantially concentrically within said coupling and said outer hose to define a continuation of said outer passage, the improvement wherein said clip means comprises a generally cylindrical one-piece C-shaped member that extends in a circular arc that is greater than 180° and having substantially concentric inner and outer surfaces respectively engaging said fitting and said coupling, said C-shaped member having opposite ends spaced from each other to define an opening means between said surfaces in communication with said outer passage on opposite sides of said clip means for fluid flow therethrough.

2. A hose assembly as set forth in claim 1 wherein said clip means has a stepped opening passing therethrough between said surfaces, and a pair of different sized tubes respectively having ends thereof disposed in said stepped opening on opposite sides of said clip means whereby said stepped opening fluidly interconnects said pair of different sized tubes together.

3. A hose assembly as set forth in claim 1 wherein said opening means is arcuate.

4. A hose assembly as set forth in claim 1 wherein said clip means has interconnecting means for interconnecting to additional structure.

5. A hose assembly as set forth in claim 4 wherein said interconnection means of said clip means comprises an opening in said clip means between said surfaces thereof.

6. A hose assembly as set forth in claim 1 wherein said clip means is formed of resilient material.

7. A hose assembly as set forth in claim 1 wherein said clip means is formed of polymeric material.

8. A hose assembly as set forth in claim 7 wherein said polymeric material is nylon.

9. A hose assembly as set forth in claim 1 wherein said clip means comprises substantially concentrically disposed inner and outer webs respectively defining said inner and outer surfaces thereof and a plurality of ribs extending between said webs and cooperating therewith to define other opening means between said surfaces that communicate with said outer passage on opposite sides of said clip means for fluid flow therethrough.

* * * * *